United States Patent
Dhawan

(10) Patent No.: US 11,724,077 B2
(45) Date of Patent: Aug. 15, 2023

(54) THERAPEUTIC SWABS FOR TREATING UPPER RESPIRATORY INFECTIONS

(71) Applicant: Subhash Dhawan, Gaithersburg, MD (US)

(72) Inventor: Subhash Dhawan, Gaithersburg, MD (US)

(*) Notice: Subject to any disclaimer, the term of this patent is extended or adjusted under 35 U.S.C. 154(b) by 0 days.

(21) Appl. No.: 17/462,070

(22) Filed: Aug. 31, 2021

(65) Prior Publication Data

US 2023/0036304 A1    Feb. 2, 2023

Related U.S. Application Data

(60) Provisional application No. 63/226,462, filed on Jul. 28, 2021.

(51) Int. Cl.
*A61M 31/00* (2006.01)
*A61J 7/00* (2006.01)

(52) U.S. Cl.
CPC .............. *A61M 31/00* (2013.01); *A61J 7/003* (2013.01); *A61M 2210/0618* (2013.01)

(58) Field of Classification Search
CPC .... A61K 2300/00; A61K 45/06; A61K 39/00; A61K 39/395; A61P 31/12; A61P 31/00; A61P 37/02; A61P 31/04; A61P 31/16; A61P 37/00; A61M 31/00; A61M 35/003; A61M 35/006; A61M 37/00; A61M 35/00
See application file for complete search history.

(56) References Cited

U.S. PATENT DOCUMENTS

| | | | | |
|---|---|---|---|---|
| 1,652,108 A | * | 12/1927 | Forbis | A61F 13/38 604/1 |
| 1,931,720 A | * | 10/1933 | Edgington | A61M 31/00 604/1 |
| 3,871,375 A | * | 3/1975 | Bennett | A61M 35/006 604/1 |

(Continued)

FOREIGN PATENT DOCUMENTS

JP      3177928 U    *    8/2012

OTHER PUBLICATIONS

El-Ghiaty, Mahmoud A et al. "Cytochrome P450-mediated drug interactions in COVID-19 patients: Current findings and possible mechanisms." Medical hypotheses vol. 144 (2020): 110033. (Year: 2020).*

(Continued)

*Primary Examiner* — Scott J Medway
(74) *Attorney, Agent, or Firm* — Knobbe Martens Olson & Bear LLP

(57) ABSTRACT

Compounds and methods for preventing or treating upper respiratory virus infections in humans and animal species are disclosed. The compounds may exhibit antimicrobial, antiviral, anti-inflammatory, anticoagulant or cytoprotective activities. The methods may deliver compounds to be delivered to the nasal and oral cavities, nasopharynx, and posterior pharynx, the primary sites of upper respiratory infections, such as influenza, SARS, and SARS-CoV-2. Therapeutic swabs comprising one or more compounds are may be used to deliver one or more compounds to deliver the above primary sites of the individuals infected with one or more upper respiratory viruses or other pathogens.

23 Claims, 2 Drawing Sheets

(56) References Cited

U.S. PATENT DOCUMENTS

| | | | | |
|---|---|---|---|---|
| 5,482,706 A * | 1/1996 | Igari | A61K 9/0019 | 424/85.1 |
| 5,846,215 A * | 12/1998 | Zygmont | A61F 13/38 | 604/1 |
| 6,350,465 B1 * | 2/2002 | Jonnalagadda | A61M 15/085 | 604/514 |
| 6,716,813 B2 * | 4/2004 | Lim | A61K 38/1729 | 514/2.5 |
| 7,582,067 B2 * | 9/2009 | Van Acker | A61M 35/006 | 604/1 |
| 8,224,438 B2 * | 7/2012 | Levin | A61N 1/36075 | 607/2 |
| 10,787,501 B1 * | 9/2020 | Babb | C07K 16/10 | |
| 10,888,606 B2 * | 1/2021 | Kim | A61P 9/00 | |
| 10,980,756 B1 * | 4/2021 | Glick | A61K 31/167 | |
| 10,987,329 B1 * | 4/2021 | Raju | A61K 31/197 | |
| 2001/0004644 A1 * | 6/2001 | Levin | A61M 15/08 | 514/646 |
| 2002/0133110 A1 * | 9/2002 | Citow | A61F 15/001 | 604/1 |
| 2003/0133877 A1 * | 7/2003 | Levin | A61K 31/445 | 128/200.23 |
| 2003/0149445 A1 * | 8/2003 | Knudson | A61F 5/56 | 606/196 |
| 2005/0058673 A1 * | 3/2005 | Scholz | A61K 45/06 | 514/557 |
| 2005/0171462 A1 * | 8/2005 | Tsaur | A61F 13/38 | 604/1 |
| 2006/0034947 A1 * | 2/2006 | Burr | A61K 36/752 | 514/738 |
| 2006/0051384 A1 * | 3/2006 | Scholz | A01N 59/00 | 424/405 |
| 2006/0052452 A1 * | 3/2006 | Scholz | A61P 11/02 | 514/731 |
| 2006/0204448 A1 * | 9/2006 | Matsuyama | A61K 31/715 | 514/10.8 |
| 2006/0253087 A1 * | 11/2006 | Vlodaver | A61M 31/00 | 604/212 |
| 2006/0257426 A1 * | 11/2006 | Baker | A61P 31/18 | 424/234.1 |
| 2007/0280900 A1 * | 12/2007 | Fox | A01N 31/02 | 424/78.37 |
| 2008/0274163 A1 * | 11/2008 | Schwartz | A61K 47/34 | 424/440 |
| 2008/0275030 A1 * | 11/2008 | Gizurarson | A61K 9/0043 | 514/772.3 |
| 2008/0287538 A1 * | 11/2008 | Scholz | A61P 31/10 | 514/552 |
| 2008/0317799 A1 * | 12/2008 | Baker | A61K 31/573 | 424/45 |
| 2009/0005339 A1 * | 1/2009 | Scholz | A61K 31/19 | 514/506 |
| 2009/0005454 A1 * | 1/2009 | Barshis | A61P 1/02 | 514/636 |
| 2009/0098207 A1 * | 4/2009 | Malakhov | A61K 9/5089 | 424/489 |
| 2009/0123540 A1 * | 5/2009 | Pipkin | A61K 31/573 | 424/468 |
| 2009/0156982 A1 * | 6/2009 | Petrie | A61K 9/127 | 604/290 |
| 2009/0162301 A1 * | 6/2009 | Tarrand | A01N 59/12 | 424/49 |
| 2009/0169286 A1 * | 7/2009 | Herweijer | A45D 34/04 | 401/145 |
| 2009/0226541 A1 * | 9/2009 | Scholz | A61P 31/04 | 424/672 |
| 2009/0291944 A1 * | 11/2009 | Ash | A01N 43/84 | 514/227.5 |
| 2010/0009970 A1 * | 1/2010 | Johansen | A61P 25/00 | 514/218 |
| 2010/0099149 A1 * | 4/2010 | Birnboim | C12Q 1/6806 | 536/23.1 |
| 2010/0179511 A1 * | 7/2010 | Rajan | A61M 11/007 | 128/200.15 |
| 2011/0097372 A1 * | 4/2011 | Rucinski | A61P 31/00 | 604/416 |
| 2011/0263646 A1 * | 10/2011 | Tarrago | A61P 11/02 | 514/314 |
| 2013/0085472 A1 * | 4/2013 | Shaari | A61M 25/10 | 604/257 |
| 2013/0123309 A1 * | 5/2013 | Ghannoum | A61K 9/00 | 514/358 |
| 2013/0338700 A1 * | 12/2013 | Matheny | A61L 31/16 | 606/199 |
| 2014/0163481 A1 * | 6/2014 | Cornell | A61M 35/003 | 604/264 |
| 2015/0238473 A1 * | 8/2015 | Dunman | A61K 31/4525 | 514/318 |
| 2015/0265752 A1 * | 9/2015 | Wei | A61K 31/66 | 514/75 |
| 2015/0297846 A1 * | 10/2015 | Given | A61K 31/192 | 128/200.14 |
| 2016/0166624 A1 * | 6/2016 | Schwartz | A61K 36/185 | 424/774 |
| 2019/0046488 A1 * | 2/2019 | Rosenblatt | C08L 5/00 | |
| 2019/0070396 A1 * | 3/2019 | Johnson | A61M 37/00 | |
| 2019/0344263 A1 * | 11/2019 | Irmscher | F04B 13/00 | |
| 2020/0237689 A1 * | 7/2020 | Peralta | A61K 47/186 | |
| 2020/0306514 A1 * | 10/2020 | Mathai | A61K 9/08 | |
| 2020/0323905 A1 * | 10/2020 | Varelas | A61K 45/00 | |
| 2021/0008150 A1 * | 1/2021 | Schinazi | C07K 5/06034 | |
| 2021/0228619 A1 * | 7/2021 | Peyman | A61K 33/242 | |
| 2021/0244705 A1 * | 8/2021 | Borody | A61P 31/00 | |
| 2021/0315742 A1 * | 10/2021 | Cicalis | A61B 10/02 | |
| 2021/0322351 A1 * | 10/2021 | Groppel | A61K 31/196 | |

OTHER PUBLICATIONS

Funes, SC et al. "Naturally Derived Heme-Oxygenase 1 Inducers and Their Therapeutic Application to Immune-Mediated Diseases." Front. Immunol. 11:1467. (Year: 2020).*

Liu, Jian et al. "Using heparin molecules to manage COVID-2019." Res Pract Thromb Haemost. 2020; 4: 518-523. (Year: 2020).*

Mahendran Ask, et al. "The Potential of Antiviral Peptides as COVID-19 Therapeutics." Front. Pharmacol. 11: 575444. (Year: 2020).*

Ohno et al. Effectiveness of topical treatment for nasopharyngitis. Oto-Rhino-Laryngology Tokyo, vol. 42, No. 1, 1999, p. 50-56. (Year: 1999).*

C.-L. Tsai, P.-C. Wu. Possible beneficial role of throat gargling in the coronavirus disease pandemic. Public Health, vol. 185, Aug. 2020, p. 45-46. (Year: 2020).*

Siegert, Scott W K, and Robert J Holt. Physicochemical properties, pharmacokinetics, and pharmacodynamics of intravenous hematin: a literature review. Advances in therapy vol. 25,9 (2008): 842-57. <https://doi:10.1007/s12325-008-0094-y> (Year: 2008).*

Olagnier, D., Farahani, E., Thyrsted, J. et al. SARS-CoV2-mediated suppression of NRF2-signaling reveals potent antiviral and anti-inflammatory activity of 4-octyl-itaconate and dimethyl fumarate. Nat Commun 11, 4938 (2020). <https://doi.org/10.1038/s41467-020-18764-3> (Year: 2020).*

Méndez-Samperio P. Peptidomimetics as a new generation of anti-microbial agents: current progress. Infection and drug resistance, 7, 229-237. (2014) <https://doi.org/10.2147/IDR.S49229> (Year: 2014).*

Loutfy MR, Blatt LM, Siminovitch KA, et al. Interferon Alfacon-1 Plus Corticosteroids in Severe Acute Respiratory Syndrome: A Preliminary Study. JAMA. (2003) 290(24):3222-3228. <https://jamanetwork.com/journals/jama/fullarticle/197895> (Year: 2003).*

Guest, Paul C., ed. Identification of Biomarkers, New Treatments, and Vaccines for COVID-19. Advances in Experimental Medicine and Biology (2021). <https://link.springer.com/content/pdf/10.1007%2F978-3-030-71697-4.pdf> (Year: 2021).*

Guest, Paul C., ed. Identification of Biomarkers, New Treatments, and Vaccines for COVID-19. Advances in Experimental Medicine and Biology (2021). Published Jul. 19, 2021. (Year: 2021).*

(56) References Cited

OTHER PUBLICATIONS

Rossi et al. Heme oxygenase-1 (HO-1) cytoprotective pathway: A potential treatment strategy against coronavirus disease 2019 (COVID-19)-induced cytokine storm syndrome. Medical Hypotheses, vol. 144, 2020, 110242. <https://doi.org/10.1016/j.mehy.2020.110242> (Year: 2020).*

Dhawan et al. "Hemin activation abrogates Mycoplasma hyorhinis replication in chronically infected prostate cancer cells via heme oxygenase-1 induction". FEBS Open Bio, Aug. 9, 2021, pp. 2727-2739.

Choi et al. "Hemin as a novel candidate for treating COVID-19 via heme oxygenase-1 induction" Scientific Reports, Nature Portfolio, Nov. 2, 2021 Article No. 21462.

International Search Report for International Application No. PCT/US2021/049986 dated Oct. 29, 2021.

* cited by examiner

THERAPEUTIC SWABS FOR TREATING UPPER RESPIRATORY INFECTIONS

CROSS-REFERENCES TO RELATED APPLICATIONS

This application claims priority to U.S. Provisional 63/226,462 filed on Jul. 28, 2021, entitled "THERAPEUTIC SWABS FOR TREATING UPPER RESPIRATORY INFECTIONS".

BACKGROUND

Field

Disclosed herein are therapeutic swabs and use thereof in a method for treating upper respiratory infections in a subject.

DESCRIPTION OF RELATED ART INCLUDING INFORMATION DISCLOSED UNDER 37 CFR 1.97 AND 1.98

Infections caused by upper respiratory pathogens, including the most dangerous novel class of COVID-19-causing coronavirus SARS-CoV-2 and its mutant variant strains, transmissible in close proximity, triggering respiratory illnesses and serious health complications, are responsible for a large number of hospitalizations and deaths every year and present a significant threat to the human health (Satia, et al. PLOS ONE. 15:e 0228544 (2020); Lai et al. Int. J. Antimicrob. Agents. 55:10593 (2020); Nakamichi et al. Scientific Reports. 11:4802 (2021).

As of Aug. 30, 2021, according to the World Health Organization, COVID-19 has affected nearly 216 million individuals worldwide claiming more than 4.5 million lives with 38.5 million infections and in excess of 631,000 deaths in the United States (World Health Organization Dashboard: Aug. 30, 2021). These numbers are increasing daily at an alarming rate.

Rapid mutational changes in SARS-CoV-2 resulting in new highly contagious and more deadly variants have worsened the pandemic, posing difficult challenges to effective treatment (Volz et al. Cell. 184:64-75 (2021); Korber et al. Cell. 184:64-75 (2021); Davies et al. Science. 372: eabg3055 (2021)).

Although vaccines are reportedly effective in reducing the severity of COVID-19 illnesses, hospitalizations, and deaths, none is yet known to prevent infections or reinfections of the vaccinated individuals by rapidly emerging highly contagious and more deadly mutant viral variants.

In addition, children, older population, and individuals with underlying health conditions, all are at a significantly higher risk of acquiring the infection and developing hyperinflammatory syndrome and other severe health complications (Toniati et al. Autoimmun. Rev. 19:102568 (2020); Gustine, J. N. & Jones, D. Am. J. Pathol. 191:4-17 (2021); Nikolich-Zugich et al. GeroScience. 342:505-514 (2020); CDC, August 2021)).

Therapeutic options for treating COVID-19 patients are limited and require hospitalizations.

The dire COVID-19 pandemic situation calls for an urgent need for safe and effective therapeutics along with convenient, preferably self-administering approaches, to treat the infected individuals at the early symptomatic stage of infection. It is critical for our own safety and also for minimizing the spread of the disease to others.

SUMMARY

This invention addresses the critical and unmet needs related to upper respiratory infections—one of which is caused by the most prevalent, highly contagious, and deadly novel coronavirus SARS-CoV-2. It is of enormous global public health concern. Accordingly, the present invention relates to the first one-of-its-kind therapeutic approach consisting of multifunctional drugs intended for their direct delivery to the nasal cavity, nasopharynx, and posterior pharynx, the primary sites of upper respiratory infection, by means of drug-adsorbed or drug-conjugated Therapeutic Swabs device system. Since epithelial cells are the primary initial target site of upper respiratory infections, delivery of the drugs exhibiting various crucial biological functions directly to the sites of infection, presents this invention as a novel multifactorial therapeutic approach. This invention offers a convenient, efficient, specific and rapid drug application on a mass-scale presenting Therapeutic Swabs device system as an ideal therapeutic modality to treat the infected individuals and to effectively control the current out-of-control deadly COVID-19 pandemic and other respiratory infections.

Figure 2:
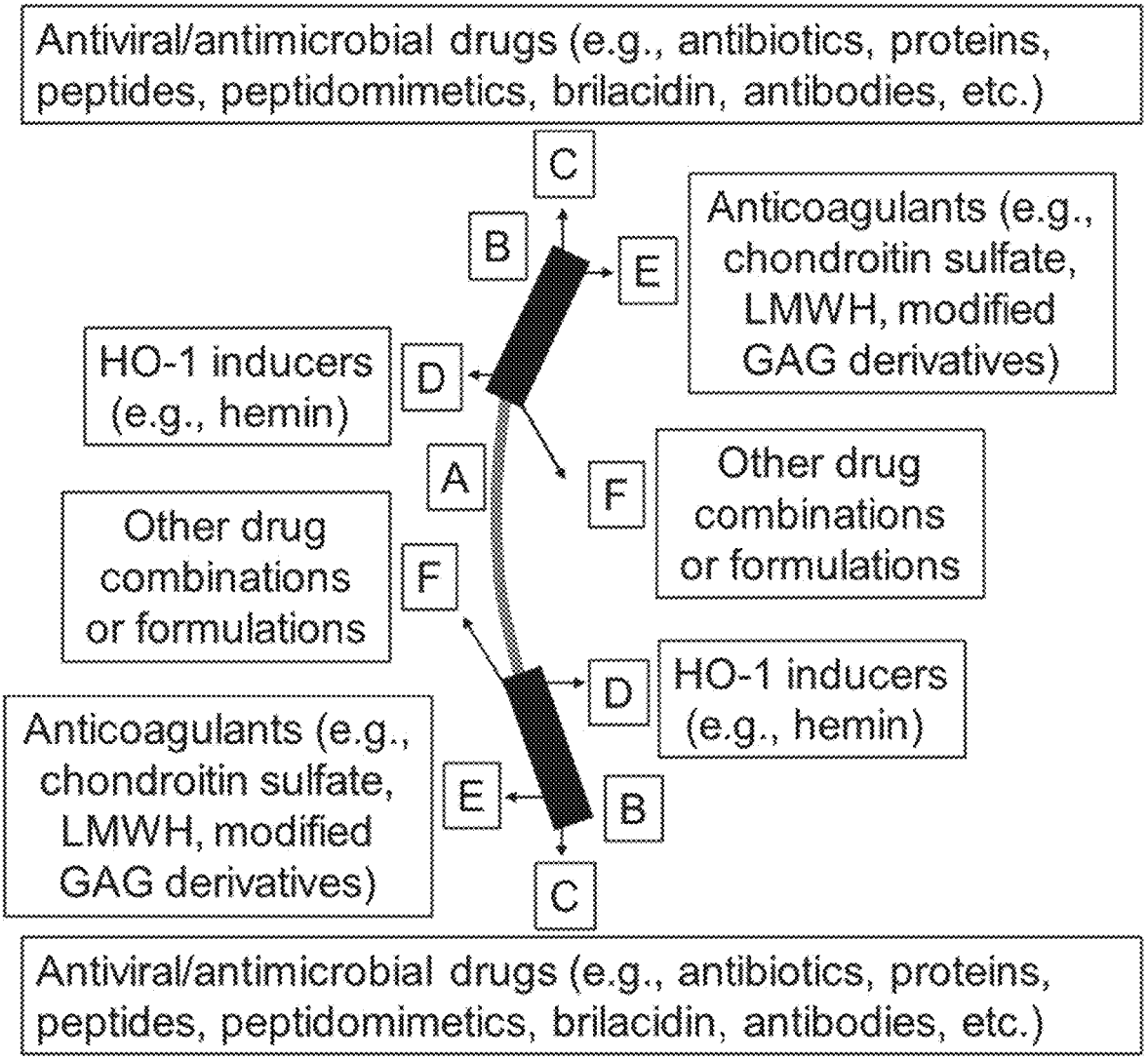
FIG. 2 illustrating the configuration of the therapeutic swabs device system comprising unique selection of drugs exhibiting crucial multiple functions depicted as [C], [D], [E] and [F] mounted on a curved or flexible stem.

Wherein:

[A] is stem made from materials meeting requirements for general safety, preferably using biodegradable materials. The curved or flexible stem shown in FIG. 2 is designed for easy access to the nasal and oral cavities in the humans and in animals;

[B] represents drug-adsorbed or drug-conjugated swabs attached on both ends of the stem [A]. If desired, only one swab on the stem of the Therapeutic Swabs may be used;

The dimensional specifications (e.g., size, appearance, material density, and physical or chemical composition) for "stem" [A] and "swabs" [B] used in the Therapeutic Swabs device system are not explicitly defined; rather, these are to be designed for drug delivery in the humans and in animals based on the anatomy of their nasal and oral cavities;

The compound [C] is an antimicrobial and antiviral agent (e.g., antibiotics, proteins, peptides, peptidomimetics, brilacidin, antibodies, etc.) with brilacidin as an example, wherein the said compound is the same drug attached, adsorbed or chemically conjugated and used in the configuration of the present invention;

The compound [C] is a different antimicrobial and antiviral drug, attached, adsorbed or chemically conjugated and used in the configuration of the present invention;

The compound [C] is absent;

The compound [D] is hemin, a strong inducer of an endogenous cytoprotective enzyme heme oxygenase-1 (HO-1), wherein the said compound is the same drug attached, adsorbed or chemically conjugated and used in the configuration of the present invention;

The compound [D] is a different inducer of HO-1, wherein the said compound is a different drug attached, adsorbed or chemically conjugated and used in the configuration of the present invention;

The compound [D] is inducer of HO-1 via upstream transcription factor Nrf2, including but not limited to, 4-octyl-itaconate and dimethyl fumarate, wherein the compound is adsorbed or chemically conjugated and used in the configuration of the present invention;

The compound [D] is absent;

The compound [E] is low molecular weight heparin (LMWH), anticoagulants, low- or non-anticoagulant heparin, and other modified glycosaminoglycans (GAG) derivatives, wherein the said compound is the same drug attached, adsorbed or chemically conjugated and used in the configuration of the present invention;

The compound [E] is a different LMWH, anticoagulants, low- or non-anticoagulant heparin, and other modified GAG derivatives wherein the said compound is different drug attached, adsorbed or chemically conjugated and used in the configuration of the present invention;

The compound [E] is a different compound possessing a net negatively charge attached, adsorbed or chemically conjugated and used in the configuration of the present invention;

The compound [E] is absent;

The "Other drug formulations" [F] is a drug, drug components, or drug combinations exhibiting antiviral, antimicrobial, cytoprotective, anti-inflammatory, and anticoagulant activities used in the configuration of the present invention;

The "Other drug formulations" [F] is a drug or drug components exhibiting antiviral activity, including but not limited to, remdesivir, favipiravir, polyclonal or monoclonal antibodies, proteins, peptides, peptidomimetics, nucleotides, etc., either individually or in any preferred combinations used in the configuration of the present invention;

The "Other drug formulations" [F] is a drug, drug components, or drug combinations exhibiting anti-inflammatory activity, including but not limited to, corticosteroids, indomethacin, other nonsteroidal anti-inflammatory drugs (NSAIDs), etc., used in the configuration of the present invention;

The compound [F] is absent.

DETAILED DESCRIPTION

Respiratory pathogens are known to primarily target the lung (Subbarao, K. & Mahanty, S. Immunity. 52:905-909 (2020)). These pathogens enter through the nasal or oral cavity. Therefore, it is desirable to target the nasal cavity, oral cavity, nasopharynx, and posterior pharynx directly where the primary infections occur to provide rapid and robust protection.

This invention relates to a therapeutic swabs device system comprising plurality of drugs possessing various crucial cellular protective functions (e.g., antiviral, antimicrobial, cytoprotective, and anti-inflammatory) intended to specifically and directly targeting the primary sites of upper respiratory infections. The approach presented in this invention not only has the potential to effectively treat upper respiratory infections, it can also reduce the risk of adverse side effects associated with high systemic absorption of drugs that are administered in the form of oral medicines or injections. The multifactorial generic antiviral therapeutic approach presented in this invention is much-warranted to control the current out-of-control COVID-19 pandemic situation.

As will be familiar to those skilled in the art, systemic administration of drugs either orally, by injections, or via other routes is not without the risk of causing adverse effects, sometimes serious in nature. The preferred embodiment of the present invention contemplates to Therapeutic Swabs device system as a therapeutic device for delivering plurality of drugs exhibiting distinct antiviral, antimicrobial and cytoprotective functions for specifically targeting the nasal cavity, nasopharynx, and throat, the primary sites of upper respiratory infections.

It will be appreciated that one or more crucial drugs are delivered simultaneously and directly to the infected sites of upper respiratory infections for maximizing their effectiveness, signifying a broader public health utility of the present invention. Accordingly, an embodiment of the present invention relates to selection of plurality of drugs possessing: (a) antiviral activity to disrupt the viruses or inhibit viral replication; (b) anti-inflammatory activity to reduce inflammation associated with viral infections; (c) cytoprotective function to prevent virus-induced cell death; (d) anticoagulant activity to reduce blood clotting in upper respiratory viral infections; and (e) bearing the net negatively charged moieties on one or more drugs to potentially bind the positively charged viruses and, as a result, protect the target cells from being infected.

The term "antiviral/antimicrobial drugs" used herein (e.g., antiviral, antimicrobial, antibiotics, proteins, peptides, peptidomimetics, antibodies, nucleotides, etc.), depicted as [C] in FIG. 1 and FIG. 2 of this invention, signifies drugs or compounds, synthetic or natural products, exhibiting antiviral or antimicrobial activity. An embodiment of the present invention relates to utility of brilacidin, a peptide or a biomimetic antimicrobial polymer derived from a host protein defensin exhibiting antiviral and antibacterial activities (Tew et al. Proc. Natl. Acad. Sci. 99:5110-5114 (2002); Ding, J., Chou, Y. Y. & Chang, T. L. J. Innate Immunity. 1:413-420 (2009); Som et al. Clin. Vaccine Immunol. 19:1784-1791 (2012); Brice, D. C. & Diamond, G. Curr. Med. Chem. 27:1420-1443 (2020); Di, Y. P. Curr. Med. Chem. 27:1385-1386 (2020); Bakovic et al. Viruses. 13:271, (2021)), depicted as [C] in FIG. 1 and FIG. 2, in the configuration of the present invention. Brilacidin may be substituted with other drugs or agents exhibiting antimicrobial characteristics.

An embodiment of the present invention specifically utilizes heme oxygenase-1 (HO-1)-inducing drugs, depicted as [D], providing a strong "generic innate cellular protection" against a wide variety of infections, regardless of types, mutants, or strains of the pathogens, such as HIV-1, Ebola virus, Vaccinia virus, Zika virus, West Nile virus, Dengue virus, even a parasite *Leishmania donovani*, and, more recently, a *mycoplasma Mycoplasma hyorhinis* (Devadas, K. & Dhawan, S. J. Immunol. 176:4252-4257 (2006); Zhou et al. Curr. Trends Immunol. 14:53-56 (2013); Dhawan, S. Curr. Trends Immunol. 14:65-70 (2013); Meseda et al. Biochem. Biophys. Res. Commun. 454:84-88 (2014); Huang et al. Curr. Trends Immunol. 17:117-123 (2016); Hill-Batorski et al. J. Virol. 87:13795-13802 (2013); Huang et al. Virology. 503: 1-5 (2017); Chi et al. J. Transl. Med. 14:35 (2016); Wagener et al. Antioxidants. 9:540 (2020); Chi et al. J. Transl. Med. 14:35 (2016); Rossi et al. Med. Hypothesis. 144:110242 (2020); Huang et al. FEBS Open Bio. Published online on Aug. 10, 2021; https://doi.org/10.1002/2211-5463.13271; Dhawan, S. Curr. Trends Immunol. 22:19-21 (2021); Dhawan, S. Curr. Trends Immunol. 22:43-47 (2021); Dhawan, S. Am. Pharm. Rev. 48-49 (May/June 2021)). Therefore, the utility of HO-1 inducers in the configuration of this invention presents a significant advancement for the general host protection against infections.

Figure 1:
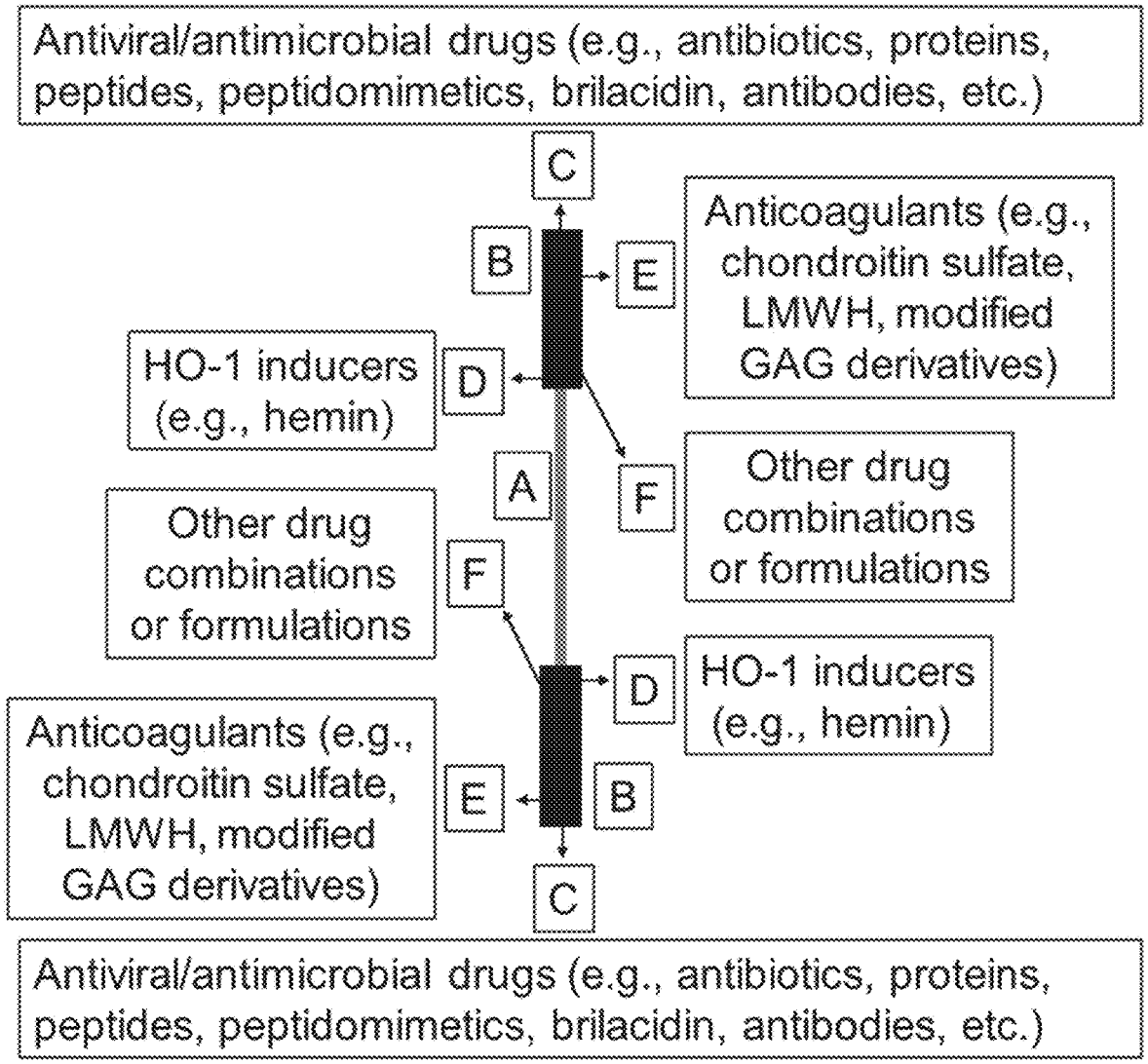
FIG. 1 illustrating the configuration of the therapeutic swabs device system comprising unique selection of drugs exhibiting crucial multiple functions depicted as [C], [D], [E] and [F] mounted on a straight stem.

It will be appreciated that hemin, depicted as [D] in FIG. 1 and FIG. 2 of this invention, is the active component of a previously FDA-approved drug Panhematin® for another indication (Siegert, S. W. & Holt, R. J. Adv. Ther. 9:842-857 (2008); therefore, this highly significant advantage rules out any serious adverse side effects of this drug that induces strong innate cytoprotective, anti-inflammatory, and antiviral functions.

The term "HO-1 inducer", including Nrf2-dependent (or independent) HO-1 inducers, depicted as [D] in FIG. 1 and FIG. 2 of this invention, signifies the agents exhibiting potent cytoprotective activity against infections that are much-needed to effectively combating and for inducing a robust innate host defense against deadly infections.

The drugs depicted as [C] and [D] in FIG. 1 and FIG. 2 of this invention, may be substituted with other drugs or agents exhibiting similar functional characteristics.

A rare blood clotting in certain COVID-19-vaccinated individuals is reported (Ledford, H. Nature 596:479-481 (2021). Whereas heparin is thought to be linked to blood clotting (cited in the above reference), non-anticoagulant heparin derivative, the low molecular weight heparin (LMWH), has been reported to elicit beneficial effects on mortality in COVID-19 by: (a) inhibition of heparinase activity; (b) reduction of chemokines and cytokines; (c) interference with leukocyte trafficking; and (d) reducing viral cellular entry (Buijsers et al. EBioMedicine. 59:102969 (2020).

Accordingly, an embodiment of the present invention is anticoagulants or low-anticoagulants, e.g., chondroitin sulfate (CS), LMWH, or modified low- or non-anticoagulant glycosaminoglycans (GAG) derivatives, including N-acetylated glycol-split heparin, and other heparin modifications, depicted as [E] in FIG. 1 and FIG. 2, providing a beneficial utility of non-anticoagulant activity or reduced anticoagulant activity in the configuration of the present invention without unwanted side effects (Duckworth et al. Oncotarget. 6:23671-23687 (2015); Casu, B., Vlodaysky, I & Sanderson, R. D. Pathophysiol. Haemost. Thromb. 36:195-203 (2009).

CS is a small molecule with molecular mass of ~463 Da as compared to heterogeneous heparin with high molecular mass ranging between 3,000 Da to 30,000 Da. Therefore, CS, LMWH or other modified GAG derivatives present better and useful alternatives for use in the configuration of this invention. In addition, the net negative charge on CS, LMWH or modified GAGs could potentially bind positively charged upper respiratory viruses, including SARS-CoV-2, to prevent their attachment to the target cells.

The low- or non-anticoagulant heparin, LMWH, or modified GAG derivatives, depicted as compound [E] in FIG. 1 and FIG. 2, may be used or replaced by other independent drug molecules possessing net negatively charged moieties.

The term "Other drug formulations" (shown as [F] in FIG. 1 and FIG. 2) used herein refers to drugs or drug components exhibiting antiviral, antimicrobial, anti-inflammatory, anticoagulant, cytoprotective, and other relevant crucial medicinal functions.

Therapeutic Swabs device system presents a significant advantage over conventional administration of antiviral and antimicrobial drugs for treating upper respiratory infections via other routes (e.g., pills, capsules, via injections, etc.) in terms of minimizing high systemic absorption of the drugs.

This invention also presents much superiority over the antiviral and antimicrobial drug administration by nasal drops or nasal sprays in terms of minimizing the dripping or spilling of the drugs and/or contaminated nasal secretions.

Collectively, this invention presents a novel configuration designed for an effective therapeutic approach for targeting specifically the infected sites of upper respiratory infections enabling a broadly applicable remedy for treating upper respiratory infections in humans and in animals.

The utility of the present invention will have a tremendous positive impact on the public health safety on a mass-scale in controlling the current COVID-19 pandemic crisis as well as in preparing us for the unforeseen future viral outbreaks. The Therapeutic Swabs device system presents a convenient and useful therapeutic tool to offer medical intervention by healthcare professionals, by other individuals, by friends and family members, by self-administration, and for home use to minimize the spread of deadly respiratory infections to others and to retard the disease progression.

What is claimed is:

1. A therapeutic swab consisting of:
   a stem having a first end and a second end;
   a first drug-loaded swab located at the first end, the first drug-loaded swab consisting of a swab and a first plurality of drugs consisting of a first composition consisting of:
   at least one antiviral agent,
   at least one heme oxygenase-1 (HO-1) inducer selected from the group consisting of hemin, 4-octyl-itaconate, dimethyl fumarate, and combinations thereof,
   an anticoagulant selected from a modified heparin, a low molecular weight heparin (LMWH), chondroitin sulfate (CS), and a modified glycosaminoglycans (GAG) derivative, and
   a drug component having anti-inflammatory activity; and
   a second drug-loaded swab located at the second end, wherein the second drug-loaded swab consists of a second plurality of drugs identical to the first composition,
   wherein the therapeutic swab is configured for use in a nasopharynx and a posterior pharynx of a subject.

2. The therapeutic swab of claim 1, wherein the stem is rigid.

3. The therapeutic swab of claim 1, wherein the stem is flexible.

4. The therapeutic swab of claim 1, wherein the antiviral agent is a protein.

5. The therapeutic swab of claim 1, wherein the antiviral agent is a peptide.

6. The therapeutic swab of claim 1, wherein the antiviral agent is a peptidomimetic.

7. The therapeutic swab of claim 1, wherein the antiviral agent is an antibody.

8. The therapeutic swab of claim 1, wherein the anticoagulant is a modified heparin.

9. The therapeutic swab of claim 1, wherein the anticoagulant is LMWH.

10. The therapeutic swab of claim 1, wherein the anticoagulant is CS.

11. The therapeutic swab of claim 1, wherein the anticoagulant is a modified GAG derivative.

12. A therapeutic swab for treating an upper respiratory infection in a subject, the therapeutic swab comprising:
    a stem having a first end and a second end;

a first drug-loaded swab located at the first end, the first drug-loaded swab consisting of a swab and a first plurality of drugs consisting of:
brilacidin,
at least one innate heme oxygenase-1 (HO-1) inducing agent selected from hemin, 4-octyl-itaconate, dimethyl fumarate, and combinations thereof,
at least one anticoagulant selected from a modified heparin, a low molecular weight heparin (LMWH), chondroitin sulfate (CS), and a modified glycosaminoglycans (GAG) derivative, and
at least one drug component having anti-inflammatory activity,
wherein the therapeutic swab is configured for use in a nasopharynx and a posterior pharynx of a subject.

13. The therapeutic swab of claim 12 further comprising a second drug-loaded swab located at the second end.

14. The therapeutic swab of claim 13, wherein the second drug-loaded swab includes a second plurality of drugs having a composition identical to the first plurality of drugs.

15. The therapeutic swab of claim 12, wherein the stem is rigid.

16. The therapeutic swab of claim 12, wherein the stem is flexible.

17. A method of treating an upper respiratory infection in a human subject, the method comprising:
locally administering a plurality of drugs located on a drug-loaded swab to at least one body region of the subject,
the at least one body region including the posterior pharynx of the human subject, and
the plurality of drugs consisting of:
at least one antiviral agent,
hemin,
an anticoagulant selected from a modified heparin, a low molecular weight heparin (LMWH), chondroitin sulfate (CS), and a modified glycosaminoglycans (GAG) derivative, and
a drug component having anti-inflammatory activity.

18. The method of claim 17, further comprising locally administering the plurality of drugs located on both ends of a double-ended drug-loaded swab to the nasal cavities, oral cavities, and nasopharynx of a subject.

19. The method of claim 17, further comprising locally administering the plurality of drugs located on both ends of a double-ended drug-loaded swab to the nasal cavities, oral cavities, or nasopharynx of the subject.

20. The therapeutic swab of claim 1, wherein the heme oxygenase-1 (HO-1) inducer is hemin, 4-octyl-itaconate, or dimethyl fumarate.

21. The therapeutic swab of claim 1, wherein the heme oxygenase-1 (HO-1) inducer is dimethyl fumarate.

22. The therapeutic swab of claim 1, wherein the heme oxygenase-1 (HO-1) inducer is 4-octyl-itaconate.

23. The therapeutic swab of claim 1, wherein the heme oxygenase-1 (HO-1) inducer is hemin.

* * * * *